United States Patent [19]
Ouchi

[11] Patent Number: 5,980,537
[45] Date of Patent: Nov. 9, 1999

[54] LIGATION DEVICE FOR ENDOSCOPE

[75] Inventor: Teruo Ouchi, Saitama-ken, Japan

[73] Assignee: Asahi Kogaku Kogyo Kabushiki Kaisha, Tokyo, Japan

[21] Appl. No.: 09/098,498

[22] Filed: Jun. 17, 1998

[30] Foreign Application Priority Data

Jun. 19, 1997 [JP] Japan .................................... 9-162141

[51] Int. Cl.$^6$ ................................................ A61B 17/04
[52] U.S. Cl. .......................................... 606/140; 606/141
[58] Field of Search ................................... 606/139–144

[56] References Cited

U.S. PATENT DOCUMENTS

| | | | |
|---|---|---|---|
| 4,178,810 | 12/1979 | Takahashi | 606/140 |
| 4,735,194 | 4/1988 | Stiegmann | 600/117 |
| 5,226,908 | 7/1993 | Yoon | 606/141 |
| 5,269,789 | 12/1993 | Chin et al. | 606/140 |
| 5,569,268 | 10/1996 | Hosoda | 606/140 |

FOREIGN PATENT DOCUMENTS

8-280699  10/1996  Japan .

*Primary Examiner*—Gary Jackson
*Attorney, Agent, or Firm*—Greenblum & Bernstein, P.L.C

[57] ABSTRACT

A ligation device includes (1) a flexible outer tube which can be inserted through a channel of an insertion tube of the endoscope, (2) a flexible inner tube provided in the outer tube, (3) a ring which is made of an elastic material and is provided to a periphery of the inner tube, and (4) a manipulator which moves the outer tube with respect to the inner tube, so that the outer tube pushes the ring out of the inner tube.

25 Claims, 7 Drawing Sheets

LIGATION DEVICE FOR ENDOSCOPE

BACKGROUND OF THE INVENTION

The present invention relates to a ligation device used in an endoscopic surgery, for tying up (ligating) a bleeding part of a mucous membrane of a human body cavity.

Conventionally, a ligation device includes a cylindrical hood which is mounted to a tip of an insertion tube of an endoscope. The hood is so constituted that the hood projects (in a inserting direction) from the tip of the insertion tube. The insertion tube has a suction channel which opens at an end surface of the tip of the insertion tube. When the hood is mounted to the insertion tube, the suction opening is surrounded by the hood.

An elastic ring is used as a ligature, that is, a member which ties up the mucous membrane. The ring is made of rubber or the like, and is mounted to an outer surface of the hood in such a manner that the ring is elastically extended. In order to push the ring out of the hood toward the mucous membrane, a movable sleeve is provided to the outer surface of the hood. The movable sleeve is slidable in the axial direction of the hood.

On ligating a mucous membrane, an operator inserts the insertion tube into the human body cavity so that the hood abuts the mucous membrane. Then, the operator starts a suction (via the suction opening), so that the mucous membrane is sucked in a hood. With this, the sucked mucous membrane forms a polyp. Further, the operator actuates the movable sleeve thereby to push the ring out of the hood, so that the ring surrounds the polyp. Once the ring surrounds the polyp, the ring is contracted due to its elasticity. With this, the polyp is tied up by the ring.

However, since the ring is conventionally provided to the outer surface of the hood, the diameter of the ring must be relatively large. Thus, it is difficult to ligate a small part such as micro blood vessels.

Further, the insertion tube has a view window which enables an operator to observe a mucous membrane. The view window is provided at an end surface of the insertion tube. However, when a suction is performed, the mucous membrane is sucked in the hood and interferes the view of the operator. That is, it is difficult for the operator to observe the mucous membrane during the ligation.

SUMMARY OF THE INVENTION

It is therefore an object of the present invention to provide a ligation device capable of ligating a small part such as a micro blood vessel.

Further, it is another object of the present invention to enable an operator to observe a mucous membrane during a ligation.

According to one aspect of the present invention, there is provided a ligation device including (1) a flexible outer tube which can be inserted through a channel of an insertion tube of the endoscope, (2) a flexible inner tube provided in the outer tube, (3) a ring which is made of an elastic material and is provided to a periphery of the tip of the inner tube, and (4) a manipulator which moves the outer tube with respect to the inner tube, so that the outer tube pushes the ring out of the inner tube.

With such an arrangement, since the ring is provided to the periphery of the inner tube (which is inserted through the channel of the insertion tube), the diameter of the ring can be small enough to ligate a small part such as micro blood vessels.

Generally, the ligation device is used with the endoscope having a view window at the end surface of the insertion tube. In such case, since the mucous membrane is sucked in the inner tube and does not interfere with the view through the view window, the operator is able to observe the mucous membrane during the ligation. Thus, it is possible to safely and accurately perform the ligation.

In a particular arrangement, the inner tube is provided with a peripheral groove formed on an outer surface of the inner tube. With this, when the ring is not pushed by the outer tube, the ring is not dropped out of the inner tube.

Preferably, the manipulator includes a first part fixed to the outer tube and a second part fixed to the inner tube. Further, the manipulator is so constituted that the first part can be moved with respect to the second part. The first part is so constituted that an operator can hook his index finger and middle finger thereto, while the second part is so constitute that the operator can hook his thumb thereto. With such an arrangement, the operation for moving the outer tube with respect to the inner tube becomes simple.

Optionally, it is possible that the manipulator has a port connected to the inner tube. By fitting a tube of a suction apparatus to the port, a suction (through the interior of the inner tube) is enabled.

In another particular arrangement, the inner tube has a large diameter portion formed at a tip thereof. In such case, the ring is located between the large diameter portion and a tip of the outer tube. It is further possible that the outer tube has at least one slit extending in the direction of the axis thereof.

DESCRIPTION OF THE PREFERRED EMBODIMENT

The embodiment of the present invention is described.

Figure 1:
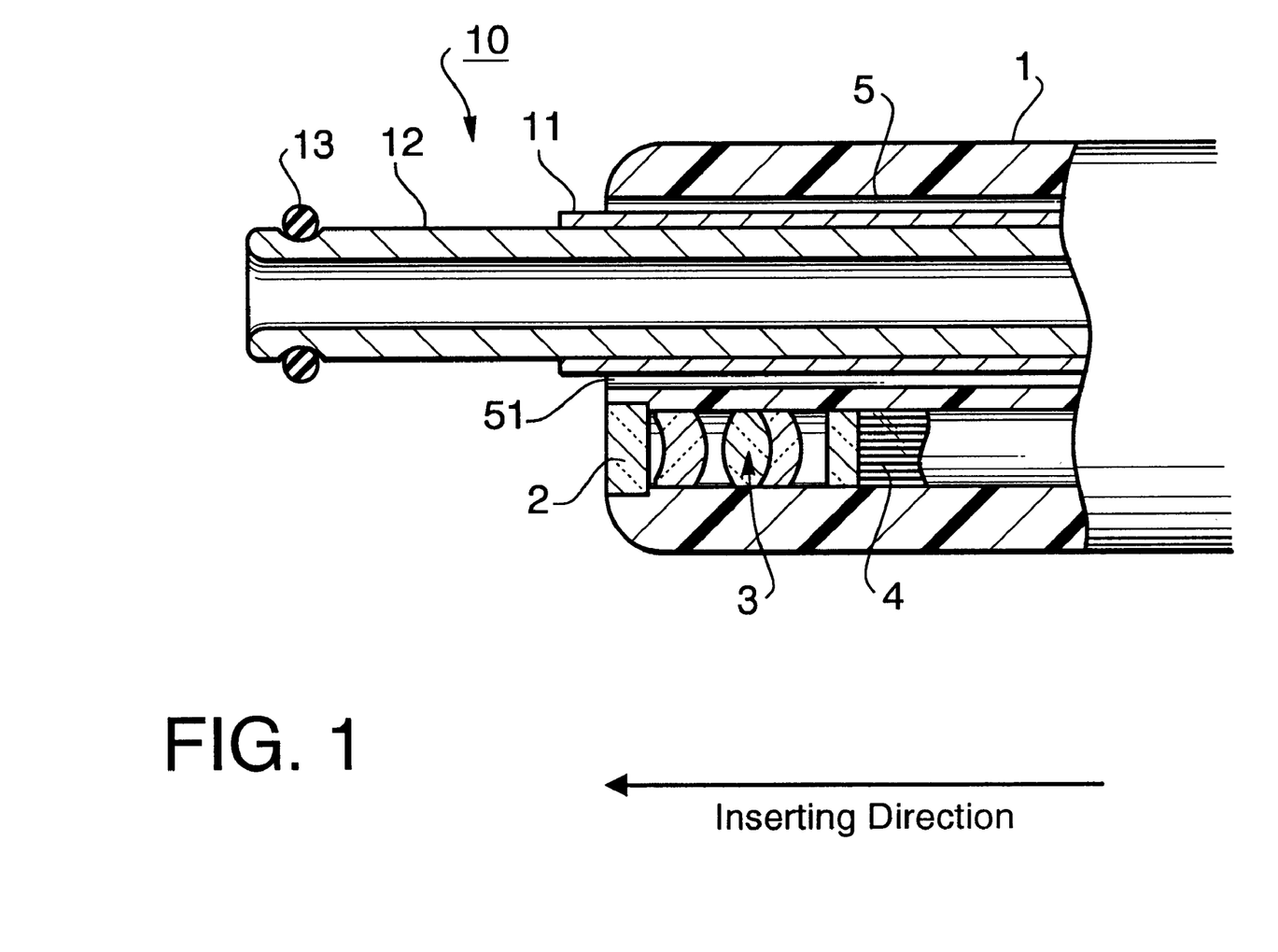
FIG. 1 is a sectional view of a ligation device according to an embodiment.

FIG. 1 is a sectional view of a insertion tube 1 of an endoscope and a ligation device 10 according to the embodiment. Hereinafter, a 'tip' is defined as a head end of the insertion tube 1 (or the ligation device 10) in the inserting direction.

The insertion tube 1 includes a suction channel 5 which extends through the insertion tube 1. The suction channel 5 has an opening 51 at an end surface of the insertion tube 1.

A view window 2 is provided at an end surface of the insertion tube 1. An object lens group 3 is located behind the view window 2. In order to capture an image viewed through the view window 2, an image guide fiber 4 is provided at an image plane of the object lens group 3. The image guide fiber 4 is extended to a not shown controller so that an operator is able to observe the image viewed through the view window 2.

Figures 2, 3:
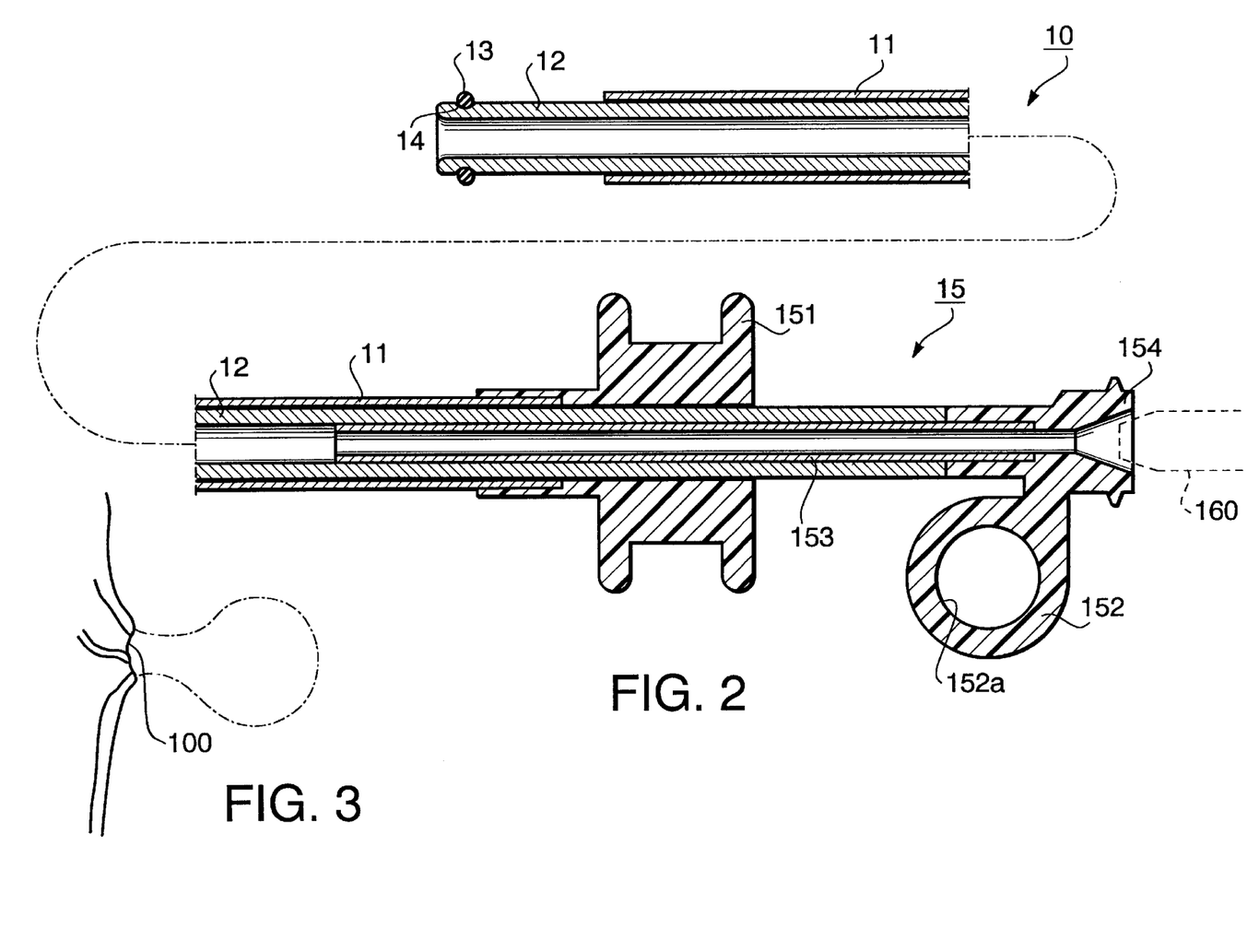
FIG. 2 is a sectional view of a insertion tube in which the ligation device of FIG. 1 is inserted.
FIG. 3 is a schematic view of a mucous membrane.

FIG. 2 is a sectional view of the ligation device. The ligation device 10 includes an outer tube 11 which can be inserted through the suction channel 5 (FIG. 1) of the insertion tube 1 (FIG. 1). The outer tube 11 is made of flexible material such as tetrafluoride ethylene. The ligation device 10 further includes an inner tube 12 provided in the outer tube 11.

A ring 13 is provided at the tip of the inner tube 12. The inner tube 12 is provided with a peripheral groove 14 which receives the ring 13. The ring 13 is made of elastic material such as rubber. In a state the ring 13 is mounted to the peripheral groove 14 of the inner tube 12, the ring 13 is elastically extended so that the ring 13 slightly ties the inner tube 12. Preferably, the inner diameter of the ring 13 (when not extended) is from 0.5 to 2.0 mm. In such case, the inner diameter of the ring 13 in a state the ring 13 is mounted to the inner tube 11 is from 2.0 to 8.0 mm. Further, the outer diameter of the ring 13 in a state said ring is mounted to the inner tube 12 is smaller than the inner diameter of the channel 5 of the insertion tube 1.

A manipulator 15 is provided for moving the outer tube 11 with respect to the inner tube 12. The manipulator 15 includes a first part 151 to which a proximal end of the outer tube 11 is fixed. The first part 151 has a through hole through which the inner tube 12 is inserted. Further, the manipulator 15 includes a second part 152 to which a proximal end of the inner tube 12 is fixed via a connecting tube 153. With this, when the first part 151 is moved with respect to the second part 152, the outer tube 11 is moved with respect to the inner tube 12. The first part 151 is so constituted that an operator can hook his index finger and middle finger thereto. The second part 152 has a hole 152a so that the operator can hook his thumb therein. With this, the operator is able to operate the manipulator 15 by one hand.

Further, the manipulator 15 includes a port 154 which is integrally provided with the second part 152. The port 154 is connected to the inner tube 12 and is able to receive a suction tube 160 of a not-shown suction apparatus. Furthermore, it is possible to insert an instrument (such as a snare, an injector or the like) through the port 154 into the inner tube 12.

Figure 4:
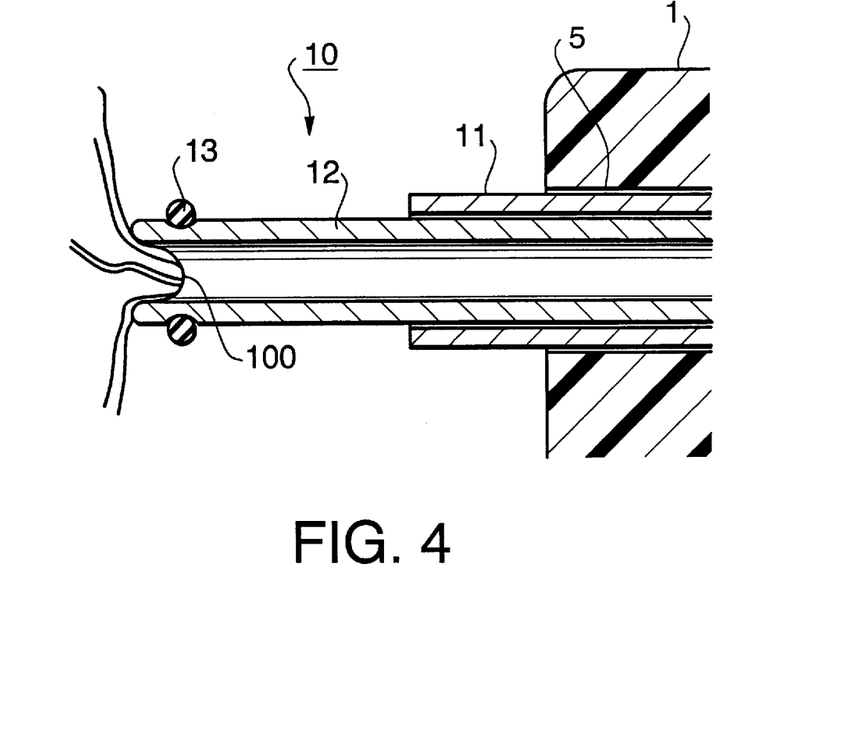
FIGS. 4, 5 and 6 are schematic views illustrating a ligation operation of the ligation device of FIG. 1.
Figure 5:
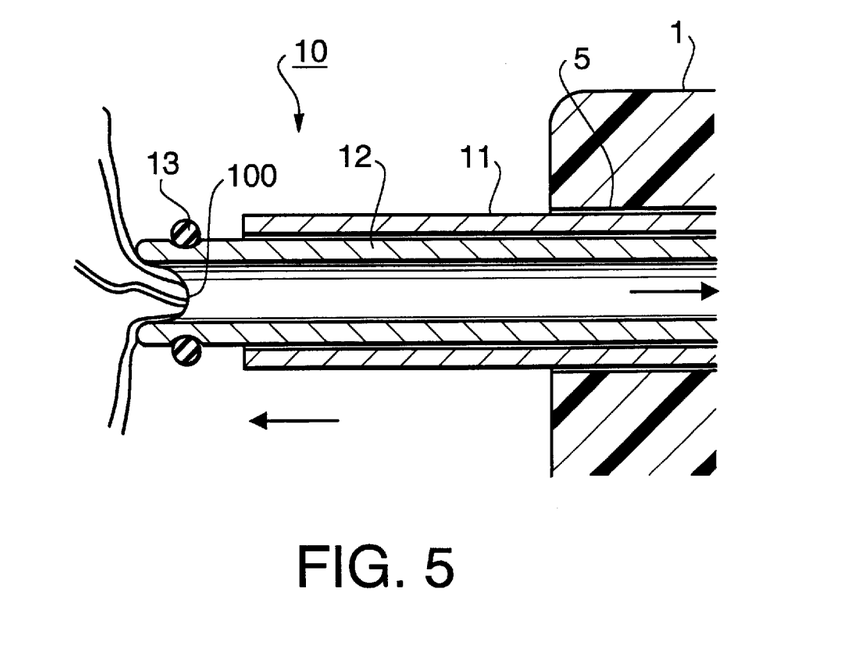
Figure 6:
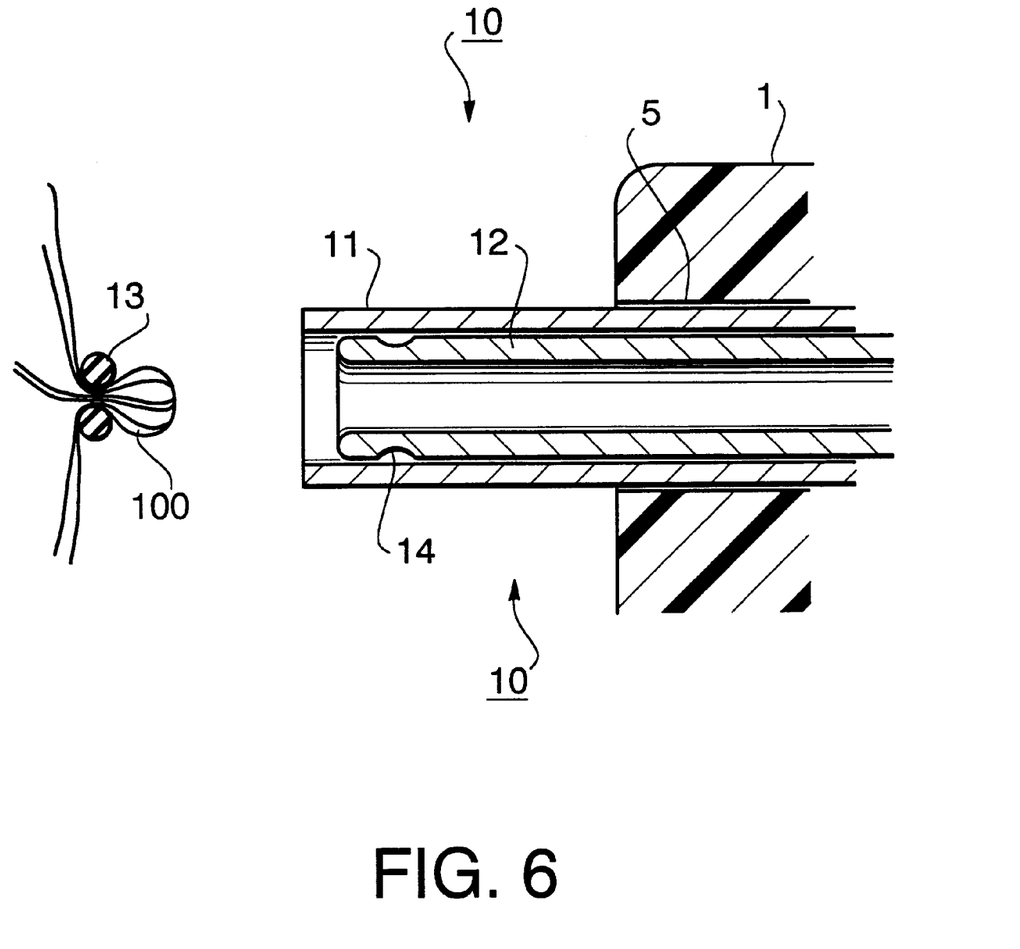

The operation of the ligation device 10 is described. The ligation device 10 is used for ligating a bleeding part of a mucous membrane as shown in FIG. 3. FIGS. 4 through 6 are sectional views illustrating a ligating operation of the ligation device 10. First, an operator connects the suction tube 160 (FIG. 2) of the not-shown suction apparatus to the port 154 (FIG. 2). As shown in FIG. 4, an operator inserts the outer and inner tubes 11 and 12 through the suction channel 5 of the insertion tube 1. Then, the operator starts suction (through the interior of the inner tube 12) by means of the not-shown suction apparatus. When the inner tube 12 is urged to the mucous membrane including a bleeding part 100, the bleeding part 100 of the mucous membrane is sucked in the interior of the inner tube 12. In this state, the sucked mucous membrane forms a polyp. Then, the operator operates the manipulator 15 (FIG. 2) so that the outer tube 11 is moved with respect to the inner tube 12 as shown in FIG. 5, thereby to push the ring 13 out of the inner tube 12. With this, the ring 13 is pushed out of the inner tube 12 to surround the polyp as shown in FIG. 6. Once the ring 13 surrounds the polyp, the ring 13 is contracted due to the elasticity. With this, the polyp is ligated by the ring 13. Finally, the operator retracts the ligation device 10 from the mucous membrane.

As described above, since the ring 13 is provided around the inner tube 12, the diameter of the ring 13 can be small enough to ligate a small part such as a micro blood vessel. Further, since the mucous membrane sucked in the inner tube 12 does not interfere with the view through the view window 2, the operator is able to observe the mucous membrane during the ligation. Thus, it is possible to safely and accurately perform the ligation.

Figure 7:
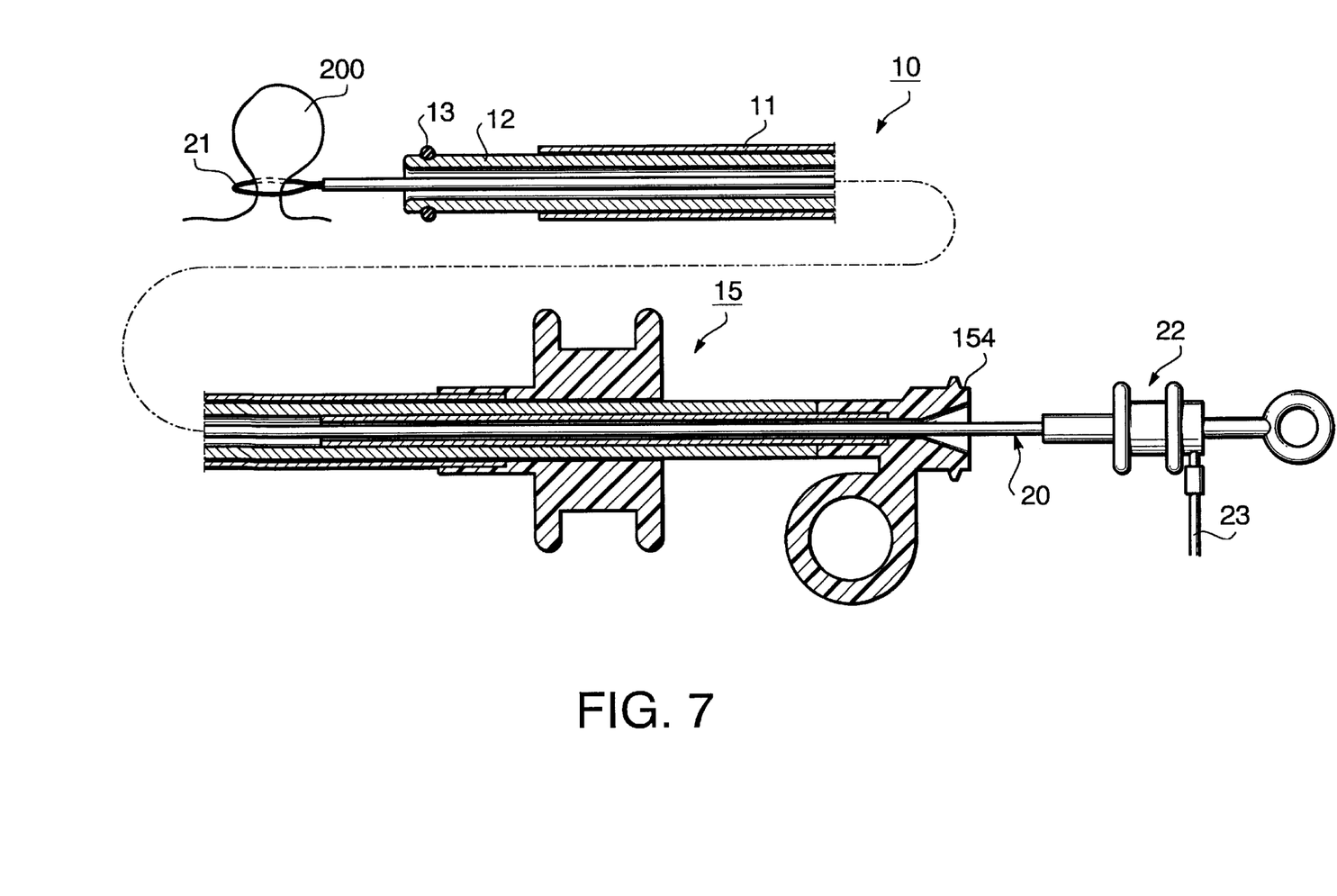
FIG. 7 is a sectional view of the ligation device in which a high-frequency snare is inserted.

In the above described embodiment, it is also possible to insert an instrument (such as a snare) through the inner tube 12 as shown in FIG. 7. In FIG. 7, a high frequency snare 20 is inserted through the inner tube 12. The snare 20 includes a snare loop 21 and an operating section 22 for opening/closing the snare loop 21. The snare loop 21 extends to the operating section 22, where the snare loop 21 is connected to a cord 23. The cord 23 is connected to a not-shown power supply. A high-frequency voltage can be applied to the snare loop 21 via cord 23.

By tying a polyp 200 with the snare loop 21 and applying a high-frequency voltage to the snare loop 21, the polyp 200 can be cut. A bleeding part (which is left after the polyp is removed) can be ligated by the ligation device 10 in a manner described above with reference to FIGS. 4 through 6.

Figure 8:
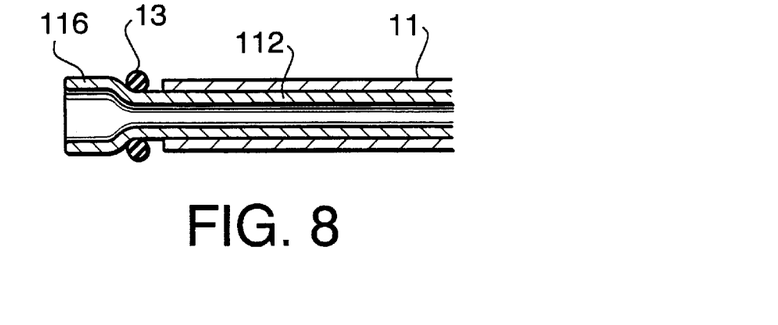
FIG. 8 is a sectional view of the ligation device including a modification of the inner tube.
Figure 9:
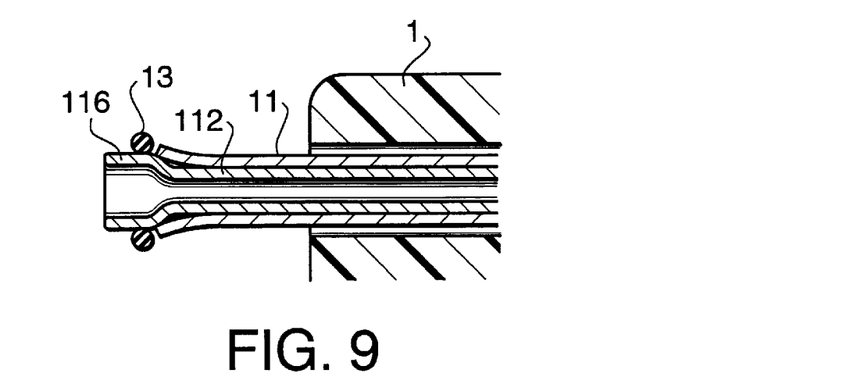
FIG. 9 is a sectional view of the insertion tube and the ligation device of FIG. 8 is inserted.

FIG. 8 shows a modification of the inner tube 12. An inner tube 112 of this modification has a large diameter portion 116 at the tip thereof. The ring 13 is provided to a portion where the diameter of the inner tube 112 is changed. When the outer tube 11 is moved to the large diameter portion 116 as shown in FIG. 9, the ring 13 is moved beyond the large diameter portion 116 and pushed out of the inner tube 112.

When the ring 13 is not pushed by the outer tube 11, the ring 13 is not dropped out of the periphery of the inner tube 112, due to the existence the large diameter portion 116. With this, it is not necessary to form a peripheral groove 14 (FIG. 1) as in the above described embodiment. Also, it is not necessary constitute the ring so that the ring 13 slightly ties the inner tube 12.

Figure 10:
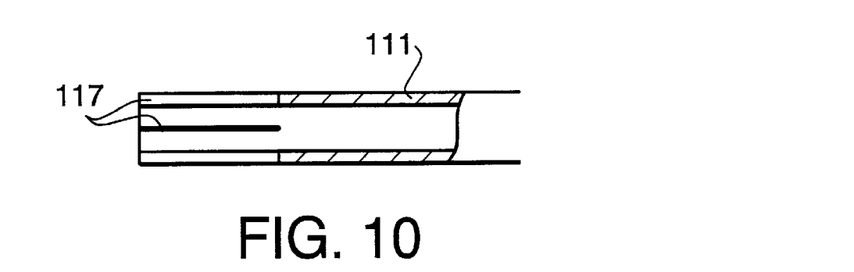
FIG. 10 is a sectional view of the modification of the outer tube.

FIG. 10 shows a modification of the outer tube 11. An outer tube 111 of this modification is used with the inner tube 112 of FIG. 8. The outer tube 111 has slits 117 extending in the axial direction thereof, so that the diameter of the outer tube 111 is easily increased. With this, the outer tube 111 easily moves to the large diameter portion 116 of the inner tube 112.

Figure 11:
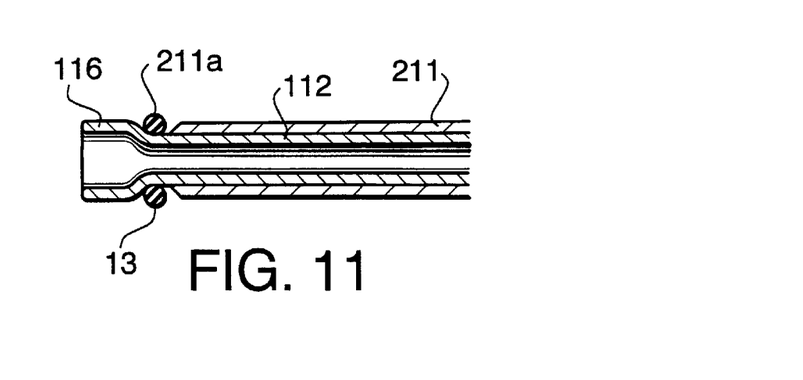
FIG. 11 is a sectional view of the ligation device including another modification of the outer tube.

FIG. 11 shows another modification of the outer tube. An outer tube 211 of this modification has a tapered edge 211a formed on an end surface of the outer tube 211. The tapered edge 211a is so formed that an outer end thereof is retracted compared with the inner end thereof. With this, when the outer tube 211 pushes the ring 13, the ring 13 is smoothly urged by the tapered edge 211a of the outer tube 211 so that the ring 13 is extended outwardly. Thus, the operation for pushing the ring 13 out of the inner tube 112 becomes easy.

Figure 12:
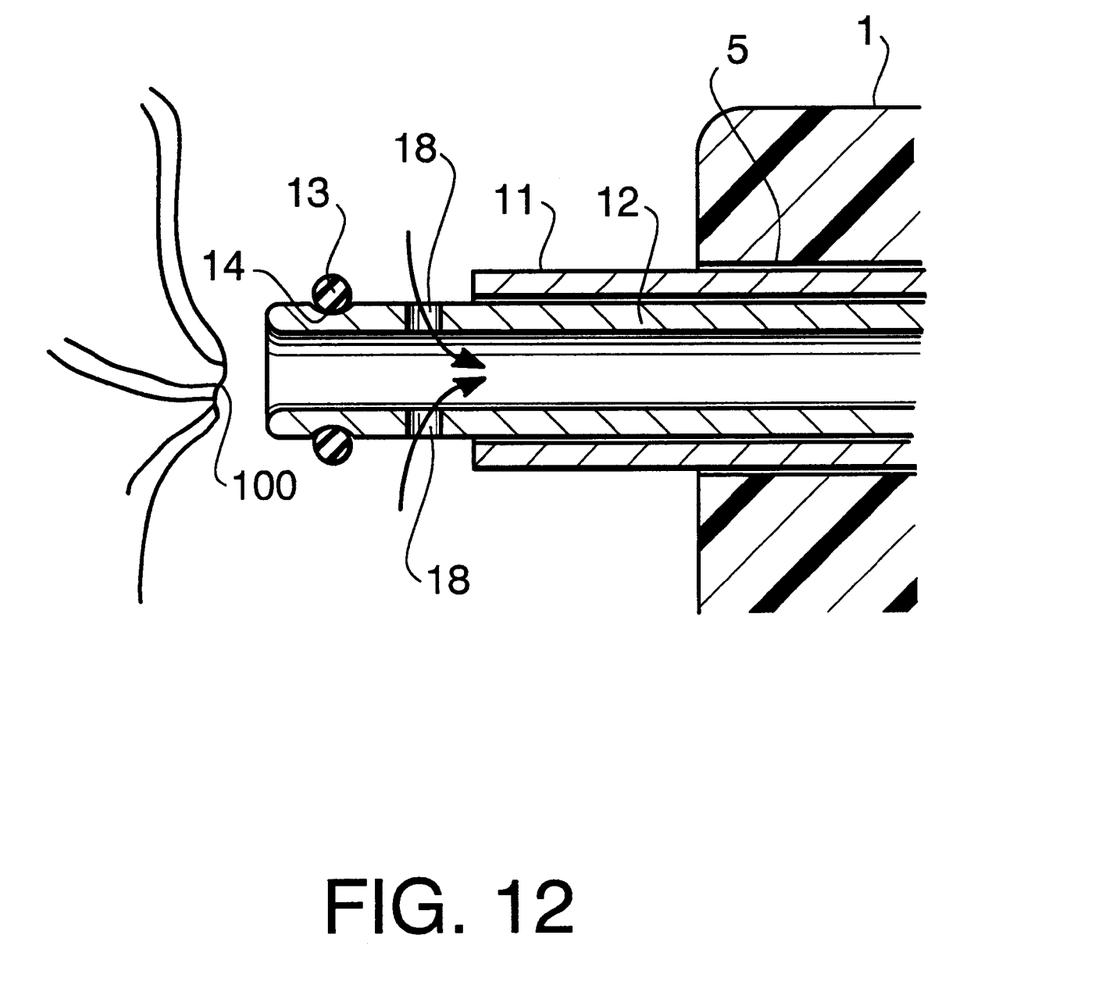
FIG. 12 is a sectional view of the ligation device including a variation of the inner tube.

FIG. 12 is a variation of the inner tube 12. In this variation, the inner tube 12 has a leak hole 18 which connects the exterior and the interior of the inner tube 12. When a suction is performed, liquid flows into the inner tube 12 through the leak hole 18, so that the mucous membrane is not sucked in the inner tube 12. When the outer tube 11 is moved to a position where the outer tube 11 covers the leak hole 18, the mucous membrane is sucked in the inner tube 12.

Such an arrangement enables an operator to perform the following operation. The operator urges the inner tube 12 several times, with the leak hole 18 opened. When the operator determines the position for urging the inner tube 12 after several trials, the operator moves the outer tube 11 toward the tip of the inner tube 12. With this, the leak hole 18 is covered, so that the sucking of the mucous membrane is started. The operator further moves the outer tube 11 toward the tip of the inner tube 12, so that the outer tube 11 pushes the ring 13 out of the inner tube 12.

Although the structure and operation of a ligation device for an endoscope is described herein with respect to the preferred embodiments, many modifications and changes can be made without departing from the spirit and scope of the invention.

The present disclosure relates to subject matters contained in Japanese Patent Application No. HEI 09-162141, filed on Jun. 19, 1997, which is expressly incorporated herein by reference in their entirety.

What is claimed is:

1. A ligation device used with an endoscope, said ligation device comprising:
    a flexible outer tube which can be inserted through a channel of an insertion tube of said endoscope;
    a flexible inner tube provided in said outer tube, wherein said inner tube is provided with a peripheral groove formed on an outer surface of said inner tube;
    a ring provided to a periphery of a tip of said inner tube, said ring being made of an elastic material; and
    a manipulator which moves said outer tube with respect to said inner tube, so that said outer tube pushes said ring out of said inner tube.

2. The ligation device according to claim 1, wherein an outer diameter of said ring in a state said ring is mounted to said inner tube is smaller than an inner diameter of said channel of said insertion tube.

3. The ligation device according to claim 1, wherein said manipulator includes first and second parts, and
    wherein said first part is fixed to said outer tube, while said second part is fixed to said inner tube.

4. The ligation device according to claim 3, wherein said manipulator is so constituted that said first part can be moved with respect to said second part.

5. The ligation device according to claim 4, wherein said first part is so constituted that an operator can hook his index finger and middle finger thereto, and
    wherein said second part is so constitute that said operator can hook his thumb thereto.

6. The ligation device according to claim 4, wherein said first part is so constituted that said inner tube slidably extends through said first part.

7. The ligation device according to claim 3, wherein said second part is provided with a port connected to said inner tube.

8. The ligation device according to claim 1, wherein said inner tube has a large diameter portion formed at a tip thereof.

9. A ligation device used with an endoscope, said ligation device comprising:
    a flexible outer tube which can be inserted through a channel of an insertion tube of said endoscope;
    a flexible inner tube provided in said outer tube;
    a ring provided to a periphery of a tip of said inner tube, said ring being made of an elastic material;
    said inner tube having a large diameter portion formed at a tip thereof, wherein said ring is located between said large diameter portion and a tip of said outer tube; and
    a manipulator which moves said outer tube with respect to said inner tube, so that said outer tube pushes said ring out of said inner tube.

10. The ligation device according to claim 9, wherein said outer tube has at least one axially extending slit.

11. The ligation device according to claim 10, wherein said outer tube has a tapered end surface, and
    wherein said tapered surface is so constituted that an outer end thereof retracts with respect to an inner end thereof.

12. A ligation device used with an endoscope, said ligation device comprising:
    a flexible outer tube which can be inserted through a channel of an insertion tube of said endoscope;
    a flexible inner tube provided in said outer tube;
    a ring provided to a periphery of a tip of said inner tube, said ring being made of an elastic material;
    a manipulator which moves said outer tube with respect to said inner tube, so that said outer tube pushes said ring out of said inner tube; and
    wherein said inner tube is provided with a hole, said hole being located so that said hole can be covered by said outer tube on the way said outer tube moves to push said ring out of said inner tube.

13. The ligation device according to claim 12, wherein a port is connected to said inner tube, said port being able to receive a tube of a suction apparatus.

14. The ligation device according to claim 13, wherein said manipulator includes a first part fixed to said outer tube and a second part fixed to said inner tube, and
    wherein said first part is movable with respect to said second part.

15. The ligation device according to claim 14, wherein said first part is so constituted that an operator can hook his index finger and middle finger thereto, and
    wherein said second part is so constituted that said operator can hook his thumb thereto.

16. The ligation device according to claim 14, wherein said port is provided to said second part of said manipulator.

17. An endoscope unit comprising an insertion tube and a ligation device;
    said insertion tube including a channel extending through said insertion tube, said insertion tube has an opening at a tip thereof;
    said ligation device comprising:
        a flexible outer tube which can be inserted through a channel of an insertion tube of said endoscope;
        a flexible inner tube provided in said outer tube, wherein said inner tube is provided with a peripheral groove formed on an outer surface of said inner tube;
        a ring provided to a periphery of a tip of said inner tube, said ring being made of an elastic material; and
        a manipulator which moves said outer tube with respect to said inner tube, so that said outer tube pushes said ring out of said inner tube.

18. The endoscope unit according to claim 17, wherein said insertion tube further includes a view window through which an operator can view an object.

19. The ligation device according to claim 17, wherein an outer diameter of said ring in a state said ring is mounted to said inner tube is smaller than an inner diameter of said channel of said insertion tube.

20. An endoscope unit comprising an insertion tube and a ligation device;

said insertion tube including a channel extending through said insertion tube, said insertion tube has an opening at a tip thereof;

said ligation device comprising:
a flexible outer tube which can be inserted through a channel of an insertion tube of said endoscope;
a flexible inner tube provided in said outer tube;
a ring provided to a periphery of a tip of said inner tube, said ring being made of an elastic material;
a manipulator which moves said outer tube with respect to said inner tube, so that said outer tube pushes said ring out of said inner tube; and
said inner tube having a large diameter portion formed at a tip thereof, wherein said ring is located between said large diameter portion and a tip of said outer tube.

21. The endoscope unit according to claim 20, wherein said insertion tube further includes a view window through which an operator can view and object.

22. The ligation device according to claim 20, wherein an outer diameter of said ring in a state said ring is mounted to said inner tube is smaller than an inner diameter of said channel of said insertion tube.

23. An endoscope unit comprising an insertion tube and a ligation device;

said insertion tube including a channel extending through said insertion tube, said insertion tube has an opening at a tip thereof;

said ligation device comprising:
a flexible outer tube which can be inserted through a channel of an insertion tube of said endoscope;
a flexible inner tube provided in said outer tube;
a ring provided to a periphery of a tip of said inner tube, said ring being made of an elastic material;
a manipulator which moves said outer tube with respect to said inner tube, so that said outer tube pushes said ring out of said inner tube; and
wherein said inner tube is provided with a hole, said hole being located so that said hole can be covered by said outer tube on the way said outer tube moves to push said ring out of said inner tube.

24. The endoscope unit according to claim 23, wherein said insertion tube further includes a view window through which an operator can view and object.

25. The ligation device according to claim 23, wherein an outer diameter of said ring in a state said ring is mounted to said inner tube is smaller than an inner diameter of said channel of said insertion tube.

* * * * *